United States Patent [19]

Lundin

[11] Patent Number: 4,674,134
[45] Date of Patent: Jun. 23, 1987

[54] EARMUFF HAVING SEALING RING INCLUDING LIQUID AND FOAM PLASTIC LAYERS

[75] Inventor: Tord R. Lundin, Billesholm, Sweden

[73] Assignee: Bilsom AB, Billesholm, Sweden

[21] Appl. No.: 843,511

[22] Filed: Mar. 25, 1986

[30] Foreign Application Priority Data

Mar. 25, 1985 [SE] Sweden .............................. 8501456-1

[51] Int. Cl.⁴ ............................................... A42B 1/06
[52] U.S. Cl. ...................................... 2/209; 381/158; 181/129
[58] Field of Search .......................... 2/209, 423, 428; 179/182 R, 156 R; 181/129; 381/158, 183

[56] References Cited

U.S. PATENT DOCUMENTS

| | | |
|---|---|---|
| 3,051,961 | 9/1962 | Clark ....................................... 2/209 |
| 3,908,200 | 9/1975 | Lundin .................................... 2/209 |
| 4,572,323 | 2/1986 | Randall ............................... 2/209 X |

*Primary Examiner*—Peter Nerbun
*Attorney, Agent, or Firm*—Burns, Doane, Swecker & Mathis

[57] ABSTRACT

An earmuff (10) has a sealing ring (20) with an outer liquid layer (38) and a foamed plastics layer (36) thereinunder. The liquid layer is arranged as a separate, annular, sheath-equipped liquid ring (38) the sheath (40) of which can move freely relative the sheath (30,32) of the sealing ring (20).

11 Claims, 2 Drawing Figures

EARMUFF HAVING SEALING RING INCLUDING LIQUID AND FOAM PLASTIC LAYERS

TECHNICAL FIELD

The present invention relates to an ear muff intended for placing over an ear for engagement against the head around the ear and including a soft, sheath-equipped sealing ring for said engagement. The earmuff in accordance with the invention is particularly intended to be included in an ear or hearing protector, e.g. of the kind which includes two earmuffs mounted on a head band.

TECHNICAL BACKGROUND

Hearing protectors of the kind mentioned above are utilized to a very great extent by persons who must spend a lot of time in noisy environments. It is very important that the hearing protector is experienced as comfortable to wear, since it will otherwise easily be "forgotten" with the accompanying risk of injury. An example of a hearing protector of this kind is described in our U.S. Pat. No. 3,908,200. Another example is described in EP-A1-127,275.

From the sound damping aspect it is essential that the earmuff sealing ring engages closely against the head everywhere round the ear. From the comfort aspect it is further essential that the sealing ring is soft and pliable and adjusts itself well to the shape of the head in a pressure—equalizing manner. With these conditions in mind the sealing ring has for a long while included foamed plastics material inside the sealing ring sheath. The foamed plastics material has very good flexibility and is furthermore light, which gives low weight of the hearing protector, something which is also of essential importance from the comfort aspect.

However, a foamed plastics-filled sealing ring has the property of being a good "heat insulator", and it therefore easily becomes unsatisfactorily "hot" where the ring engages against the head. Liquid-filled sealing rings have been proposed in an attempt to solve this problem. The liquid provides a cooling effect which is experienced positively by many. Filling with liquid also involves problems, however, since the weight of the hearing protector increases substantially and since requirements for leak proof and puncture—proof nature of the sealing ring sheath increase. Some persons also experience the liquid-filled sealing rings as less soft and comfortable than the formed plastics filled sealing rings. It has also been found that the liquid-filled sealing rings have not come to be as dominating as was expected.

OBJECT OF THE INVENTION

The object of the present invention is to provide an earmuff with a new sealing ring embodiment or structure, which substantially combines the positive properties of both discussed sealing ring types, simultaneously as the negative properties of the respective ring have been substantially removed, while retaining good sound-damping effect on utilization in hearing protectors. Accordingly, the need of manufacturing two types of earmuff, i.e. one with a liquid-filled sealing ring and one with a foamed plastics-filled sealing ring, would be dispensed with.

SUMMARY OF INVENTION

The above-mentioned object is achieved in accordance with the invention by an earmuff of the kind described in the introduction, which has the characterizing features disclosed in the accompanying claims, as well as by a new, improved sealing ring embodiment or structure.

The earmuff in accordance with the invention is thus distinguished essentially in that its sealing ring has an outer liquid ring layer, i.e. one intended for engagement against the head, and inwards thereof a foamed plastics ring layer, i.e. towards the juncture with the rest of the earmuff. This ring layer combination has been found to have extremely good comfort properties while retaining the properties of the sealing ring necessary for sound damping. The liquid layer may be made comparatively thin, as is required from the weight aspect, but with retained "cooling effect". On the other hand it should be emphasized here that a solitary thin liquid layer has been found unable to give the desired sealing effect, due to limited deformation ability. The foamed plastics layer behind the liquid layer has been found to be a yielding base allowing very good sealing ring adjustment to the head with a substantially uniform adjusted thickness of the liquid layer round the sealing ring. The sealing ring adjustment and engagement pressure equalization have also been found to be at least just as good as with foamed plastics-filled sealing rings. The good adjusting ability and engagement pressure equalization would appear to be, inter alia a result of the double adjustment availability which resides in that both the liquid layer and the foamed plastics layer yield individually, although the yielding properties are different for both layers.

A typically suitable liquid layer thickness is about 5 mm, and the liquid layer can typically constitute from about $\frac{1}{3}$ to about $\frac{1}{2}$ of the total sealing ring thickness. The liquid may typically be based on glycerine, The foamed plastics may typically have a density of about 30 kg/m$^3$ and suitably have open cells.

In accordance with the invention, the liquid layer is advantageously enclosed in a separate soft annular sheath, which is preferably at least substantially freely movable relative the soft outer sheath of the sealing ring. In other words, the liquid layer is protected in three directions inside double sheath walls. In the fourth direction (backwards) the liquid sheath engages against the foamed plastics layer, which constitutes extra protection. The risk of liquid leakage is consequently very small.

The foamed plastics layer preferably lies freely and open inside the outer sheath of the sealing ring, suitably between the liquid ring and a reinforced bottom portion on the sealing ring sheath, the bottom portion facilitating fitting and retaining the sealing ring in the earmuff.

The construction with a separate liquid ring resting on a free foamed plastics layer inside an outer sheath which is closed, except for one or some small perforations allowing the passage of air into and out of the sealing ring, has been found to give particularly good elasticity, adjustment and sound damping properties.

It has been found advantageous to make both the liquid ring layer and the foamed plastics ring layer generally plate-like, preferably with a generally rectangular cross section. The layers are suitably given essentially the same extension in the plane of the plate, i.e. the inward or rear bottom surface of the liquid ring corresponds to the forward or outer upper surface of the foamed plastics ring. Taken together, the two layers substantially fill out the sealing ring sheath.

In summary, it may be established that the new earmuff in accordance with the invention has been found to have surprisingly good comfort properties with retained good sound damping ability, these comfort properties ensuring that the inventive earmuff is experienced as being very comfortable to wear by persons who previously could only accept earmuffs with foamed plastics-filled rings, as well as by persons who previously could only accept earmuffs with liquid-filled sealing rings.

The earmuff in accordance with the invention will be described in more detail hereinafter, by way of an embodiment example and with reference to the accompanying drawings.

DESCRIPTION OF EMBODIMENT

Figure 1:
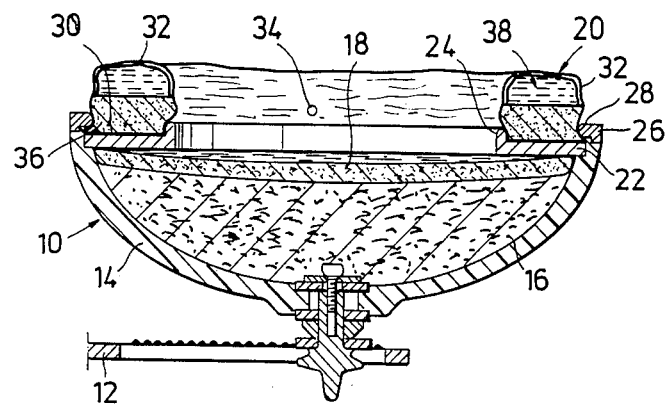
FIG. 1 is a schematic, sectional view of a headband-carried earmuff in accordance with the invention.
Figure 2:
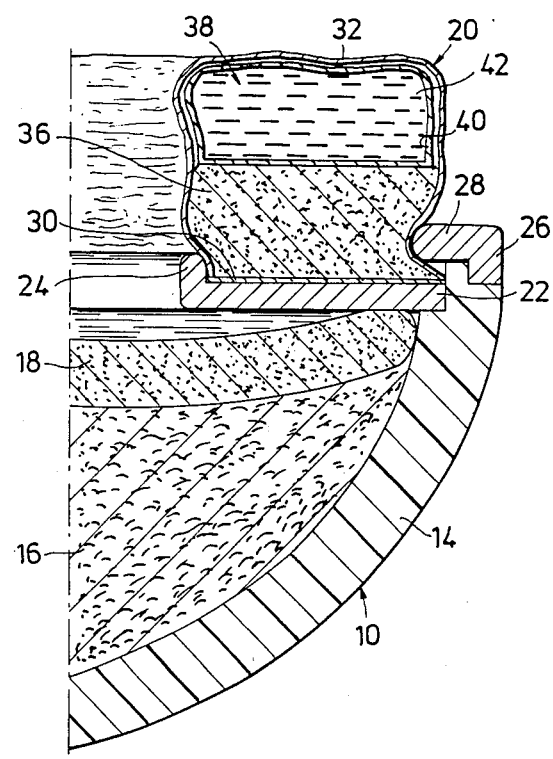
FIG. 2 is a schematic, enlarged, partial sectional view of the earmuff in FIG. 1, more closely illustrating the construction of the sealing ring included in the earmuff.

The hearing protector illustrated in FIGS. 1 and 2 is of the general kind described in our previously mentioned U.S. Pat. No. 3,908,200, to which we refer in respect of closer construction details. The protector includes two earmuffs, of which only one 10 is illustrated in FIG. 1, the earmuffs being mounted conventionally on an elastic headband 12.

The earmuff 10 includes an oval, bowl-shaped plastics shell 14 with an absorbent material 16 arranged therein, a foamed plastics layer 18 covering the absorbent, an oval sealing ring 20 and means for removably fitting the sealing ring 20 to the earmuff, including an annular fitting plate 22 with an inward bent-up flange 24 and an outer flange 26 with a projection 28 thrusting in towards the sealing ring, the function of this projection being more specifically explained in our above-mentioned U.S. patent.

The sealing ring 20 has an outer sheath comprising a stiffer annular bottom plate 30, intended for connection to, and retention at the annular plate 22, and a sheath portion 32 of thin soft plastics material having a substantially inverted U-shaped cross section. The sealing ring outer sheath 30,32 is entirely closed off, with the exception of a small hole 34 in the portion 32 for enabling air to pass into and out of the sealing ring in conjunction with deformation thereof.

Inside the sealing ring 20 and closest to the bottom plate 30 there is a foamed plastics ring 36, the width of which corresponds to that of the sealing ring 20 and which has a height corresponding to about 55-60% of the sealing ring height in an unloaded condition. The foamed plastics ring 36 thus has an essentially rectangular cross section.

Outside the foamed plastics ring 36 there is a separate liquid ring 38, filling out the rest of the interior of the sealing ring 20 and also having substantially rectangular cross section with the same width as that of the foamed plastics ring. The liquid ring 38 has a separate annular sheath 40 of thin soft plastics material enclosing the liquid 42, which is suitably glycerine of a commercial quality. The liquid ring 38 is disposed freely, i.e. it is not bonded or coupled to the sheath portion 32 or the foamed plastics ring 36. The liquid ring sheath 40 will thus be able to adjoint and 36. The liquid sheath 40 will thus be able to adjoin and follow the outer sheath portion 32, but just as well be able to move relative the latter if required. It will be further understood that the liquid ring 38 is carried by the foamed plastics ring 36 such that the greatest possible flexibility and adjustment capacity is obtained. It is particularly advantageous here that due to its resilience the foamed plastics ring enables the liquid ring 38 to deflect in a favourable manner so that good adjustment and sealing against the wearer's head is achieved.

I claim:

1. Earmuff apparatus particularly suited for a hearing protector, comprising two earmuffs mounted on a headband, said earmuff being adapted to be placed over an ear to engage against the head around the ear and including a pliable sealing ring provided with a first sheath, the sealing ring including within the first sheath a liquid layer and an annular foamed plastic layer, said liquid layer atop said foamed plastic layer so that upon applying the earmuff to the head of the user the liquid layer is nearer to the head than said foamed plastic layer said liquid layer enclosed in a second annular sheath separate of said first sheath, whereby said liquid layer is substantially freely movable relative to said first sheath.

2. The earmuff apparatus as claimed in claim 1, wherein the foamed plastic layer lies freely inside the first sheath of the sealing ring, whereby said liquid layer and said foamed plastic layer may yield independently.

3. The earmuff apparatus as claimed in claim 1, wherein the first sheath of the sealing ring is perforated so that air can flow into and out of the sealing ring.

4. The earmuff apparatus as claimed in claim 1, wherein the liquid layer and the foamed plastic layer have generally planar radial surfaces.

5. The earmuff apparatus as claimed in claim 4, wherein the liquid and foamed plastic layers each have a generally rectangular cross section.

6. The earmuff as claimed in claim 4, wherein the liquid and foamed plastic layers are coextensive with each other along a radial plane.

7. Sealing ring suitable for use in an earmuff of an ear protector, said sealing ring including a first sheath and a yieldable material arranged in the first sheath, said yieldable material including a liquid layer and a foamed plastic layer, said liquid layer located atop said foamed plastics layer so that upon applying the earmuff to the head of a user, said liquid layer is nearer to the head than the foamed plastic layer;

the liquid layer being enclosed in a second annular sheath which is separate of the first sheath so as to be unfixed relative to the first sheath, the foamed plastic layer separate of the first sheath of the sealing ring.

8. The earmuff apparatus as claimed in claim 2, wherein the first sheath of the sealing ring is perforated so that air can flow into and out of the sealing ring.

9. The earmuff apparatus as claimed in claim 2, wherein the liquid layer and the foamed plastic layer have generally planar radial surfaces.

10. The earmuff apparatus as claimed in claim 3, wherein the liquid layer and the foamed plastic layer have generally planar radial surfaces.

11. The earmuff apparatus as claimed in claim 5, wherein the liquid and foamed plastic layers are coextensive with each other on a radial plane.

* * * * *